(12) United States Patent
Shewmaker et al.

(10) Patent No.: US 6,664,109 B2
(45) Date of Patent: Dec. 16, 2003

(54) TRANSFORMATION SYSTEM WITH TI OR RI PLASMID

(75) Inventors: Christine K. Shewmaker, Woodland, CA (US); Daniel G. Facciotti, Davis, CA (US)

(73) Assignee: Calgene LLC, Davis, CA (US)

( * ) Notice: Subject to any disclaimer, the term of this patent is extended or adjusted under 35 U.S.C. 154(b) by 0 days.

(21) Appl. No.: 10/093,804

(22) Filed: Mar. 8, 2002

(65) Prior Publication Data

US 2002/0170096 A1 Nov. 14, 2002

Related U.S. Application Data

(63) Continuation of application No. 07/526,123, filed on May 21, 1990, now abandoned, which is a continuation of application No. 07/267,685, filed on Nov. 2, 1988, now abandoned, which is a continuation of application No. 06/692,605, filed on Jan. 17, 1985, now abandoned.

(51) Int. Cl.$^7$ .......................... C12N 15/84; C12N 5/04; C12N 5/10

(52) U.S. Cl. ................. 435/469; 435/415; 435/418; 435/419; 800/278; 800/287; 800/288; 800/312

(58) Field of Search ............................. 435/415, 418, 435/419, 469; 800/278, 287, 288, 312

(56) References Cited

U.S. PATENT DOCUMENTS

| | | | |
|---|---|---|---|
| 4,940,838 A | 7/1990 | Schilperoort et al. | |
| 4,962,028 A | 10/1990 | Bedbrook et al. | |
| 5,034,322 A | 7/1991 | Rogers et al. | |
| 6,020,539 A | 2/2000 | Goldman et al. | |

FOREIGN PATENT DOCUMENTS

| | | |
|---|---|---|
| EP | O-176-112 | 6/1985 |
| EP | 0 176 112 | 6/1985 |
| EP | 0 116 718 | 5/1990 |
| EP | 0 159 418 | 9/1990 |
| WO | WO 86/03776 | 7/1986 |

OTHER PUBLICATIONS

Broglie et al., "Structural Analysis of Nuclear Genes Coding for the Precursor to the Small Subunit of Wheat Ribulose-1, 5-Biosphospate Carboxylase," *Biotechnology*, 1:55-61 (1983).
Bytebier et al. "T-DNA Organization in Tumor Cultures and Transgenic Plants of the Monocotyledon *Asparagus officinalis*," *Proc. Natl. Acad. Sci., USA*, 5345-5349 (1987).
Chee et al., "Transformation of Soybean (*Glycine max*) by Infecting Germinating Seeds with *Agrobacterium tumefaciens*," *Plant Physiol.* 91:1212-1218 (1989).
Chilton et al., "*Agrobacterium rhizogenes* Inserts T-DNA into the Genomes of the Host Plant Root Cells," *Nature*, 295:432-434 (1982).
Christianson et al., "A Morphologically Competent Soybean Suspension Culture," *Science*, 222: 632-634 (1983).
Christou et al., "Opine Synthesis in Wild-Type Plant Tissue," *Plant Physiol.*, 82:218-221 (1986).
De Block et al., "Expression of Foreign Genes in Regenerated Plants and in their Progeny," *EMBO J.*, 3:1681-1689 (1984).
De Cleene and DeLey, "The Host Range of Crown Gall," *Botanical Review*, 42:389-466 (1976).
De Cleene et al., "The Host Range of Infectious Hairy--Root," Botanical Rev., 47:147-194(1981).
De Cleane, M., "The Susceptibility of Monocotyledons to *Agrobacterium tumefaciens*," *Phytopath. Z.*, 113:81-89 (1985).
DeGreve et al., "Regeneration of Normal and Fertile Plants That Express Octopine Synthase, From Tobacco Crown Galls After Deletion of Tumour-Controlling Functions," *Nature*, 300:752-755 (1982).
Deng, W-Y, "*Agrobacterium tumefaciens* Can Transform Triticum aestivum and Hordeum vulgare of Gramineae," Science (China), 33:27-33 (1990).
Facciotii et al., "Light-Inducible Expression of a Chimeric Gene in Soybean Tissue Transformed with Agrobacterium," *Biotechnology*, 3:241-246 (1985).
Flavell et al., "Prospects for Transforming Monocot Crop Plants," *Nature*, 307:108-109 (1984).
Fraley et al., "Expression of Bacterial Genes in Plants," *Proc. Natl. Acad. Sci. USA*, 80:4803-4807 (1983).
Framond et al., "Mini-Ti Plasmid and a Chimeric Gene Construct: New Approaches to Plant Gene Vector Construction," Adv. in Gene Technology: Cellular Genetics of Plants and Animals, 159-169 (1986).
Goodman et al., "Gene Transfer in Crop Improvement," *Science*, 236:48-54 (1987).
Graves et al., "The Transformation of Zea mays Seedlings with *Agrobacterium tumefaciens*," *Plant. Mol. Bio.*, 7:43-50 (1986).
Grimsley et al., "Agrobacterium-Mediated Delivery of Infectious Maize Streak Virus Into Maize Plants," *Nature*, 325:177-179 (1987).
Hernalsteens et al., "An Agrobacterium-Transformed Cell Culture from the Monocot Asparagus officinalis," *EMBO J.*, 3:3039-3041 (1984).
Herrera-Estrella et al., "Light-Inducible and Chloroplast-Associated Expression of a Chimaeric Gene Introduced into Nicotiana tabacum Using a Ti Plasmid Vector," *Nature*, 310:115-120 (1984).

(List continued on next page.)

Primary Examiner—David T. Fox
(74) Attorney, Agent, or Firm—Marshall, Gerstein & Borun LLP

(57) ABSTRACT

Novel DNA constructs are provided which are functional in soybean plants and provide for expression in soybean plant cells. Particularly, the constructs include a promoter region, as exemplary, the soybean small subunit of ribulose-1,5-bisphosphate carboxylase, an endogenous or exogenous gene other than the normal structural gene associated with the promoter, and a sequence for integration into the plant genome, such as Ri- or Ti-plasmid.

8 Claims, No Drawings

OTHER PUBLICATIONS

Herrera–Estrella et al., "Expression of Chimaeric Genes Transferred into Plant Cells Using a Ti–Plasmid–Derived Vector", *Nature*, 303:209–213 (1983).

Herrera–Estrella et al., "Chimeric Genes as Dominant Selectable Markers in Plant Cells," *EMBO J.*, 2:987–995 (1983).

Hiei et al., "Efficient Transformation of Rice (*Oryza sativa* L.) Mediated by Agrobacterium and Sequence Analysis of the Boundaries of the T–DNA," *The Plant J.*, 6:271–282 (1994).

Hiei et al., "Transformation of Rice Mediated by *Agrobacterium tumefaciens*," *Plant Mol. Biol.*, 35:205–218 (1997).

Hille et al., "Construction and Application of R Prime Plasmids, Carrying Different Segments of an Octopine Ti Plasmid from *Agrobacterium tumefaciens*, for Complementation of vir Genes," *Plasmid*, 7:107–118 (1982).

Hoekema et al.,"A Binary Plant Vector Strategy Based on Separation of vir–and T–region of the *Agrobacterium tumefaciens* Ti–plasmid," *Nature*, 303:179–180 (1983).

Hooykas–Van Slogteren et al., "Expression of Ti–Plasmid Genes in Monocytledonous Plants Infected with *Agrobacterium tumefaciens*," *Nature*, 311:763–764 (1984).

Hooykas et al., "Molecular Mechanism of Ti Plasmid Mobilization by R Plasmids: Isolation of Ti Plasmids with Transposon–Insertions in *Agrobactetium tumefaciens*," *Plasmid*, 4:64–75 (1980).

Horsch et al., "Inheritance of Functional Foreign Genes in Plants," *Science*, 223:496–498 (1984).

Jordan et al., "Transformed Callus Does Not Necessarily Regenerate Transformed Shoots," *Plant Cell Reports*, 7:285–287 (1988).

Kartha et al., "Regeneration of Pea (*Pisum sativum* L.) Plants from Shoot Apical Meristems," *Z. Pflanzenphysiol. Bd.*, 72:172:176 (1974).

Leemans et al., "Site–Specific Mutagenesis of Agrobacterium Ti Plasmids and Transfer of Genes to Plant Cells," *J. Mol. Appl. Gen.*, 1:149–164 (1981).

Lippincott et al., "The Genus Agrobacterium," The Prokaryotes Handbook on Habitats, Chapter 68 (1981).

Lu et al., "Isolation and Culture of Protoplasts of *Panicum maximum* Jacq. (Guinea Grass): Somatic Embryogenesis and Plantlet Formation," *Z. Pflanzenphysiol. Bd.*, 104:311–318 (1981).

May et al., "Generation of Transgenic Banana (*Musa acuminata*) Plants via Agrobacterium–Mediated Transformation," *Bio/Technology*, 13:486–492 (1995).

Pederson et al., "Induction and in vitro Culture of Soybean Crown Gall Tumors," *Plant Cell Reports*, 2:201–204 (1983).

Potrykus et al., "Direct Gene Transfer to Cells of a Graminaceous Monocot," *Mol. Gen. Genet.*, 199:183–188 (1985).

Potrykus et al., "Gene Transfer to Cereals: An Assessment," *Bio/Technology*, 8:535–542 (1990).

Potrykus, I, "Gene Transfer to Plants: Assessment and Perspectives," *Physiologia platarum*, 79:125–134 (1990).

Potrykus, I, "Gene Transfer to Plants: Assessment of Published Approaches and Results," *Ann. Rev. Plant Physiol. Plant Mol. Biol.*, 42:205–225 (1981).

Ritchie et al., "*Agrobacterium tumefaciens*–Mediated Expression of gusA in Maize Tissues," *Transgenic Res.*, 2:252–265 (1993).

Rothstein et al., "Promoter Cassettes, Antibiotic–Resistance Genes, and Vectors for Plant Transformation," *Gene*, 53:153–161 (1987).

Schäfer et al., "T–DNA Integration and Expression in a Monocot Crop Plant After Induction of Agrobacterium," *Nature*, 327:529–532 (1987).

Schell et al., "The Ti Plasmid as Natural and as Practical Gene Vectors for Plants," *Biotechnology*, 175–180 (1983).

Schreier et al., "The Use of Nuclear–Encoded Sequences to Direct the Light–Regulated Synthesis and Transport of a Foreign Protein into Plant Chloroplasts," *EMBO J.*, 4:25–32 (1985).

Tepfer, "Transformation of Several Species of Higher Plants by Agrobacterium rhizogenes: Sexual Transmission of the Transformed Genotype and Phenotype," *Cell*, 37:959–967 (1984).

Van Haute et al., "Intergeneric Transfer and Exchange Recombination of Restriction Fragments Cloned in pBR322: A Novel Strategy for the reversed genetics of the Ti Plasmids of *Agrobacterium tumefaciens*," *EMBO J.*, 2:411–417 (1983).

Van Montagu et al., "The Ti Plasmids of Agrobacterium," *Current Topics in Microbiology and Immunology*, 96:238–254 (1982).

Van Veen et al., "Mechanisms of Tumorigenesis by *Agrobacterium tumefaciens*," 19–21 (1988).

White and Nester, "Relationship of Plasmids Responsible for Hairy Root and Crown Gall Tumorgenicity," *J. Bact.*, 144:710–720 (1980).

Wilmink, et al., "Expression of the GUS–gene in the monocot tulip after introduction by particle bombardment and Agrobacterium," *Plant Cell Reports*, 11:76–80 (1992).

Zambryski et al., "Ti–Plasmid Vector for the Introduction of DNA into Plant Cells without Alteration of their Normal Regeneration Capacity," *EMBO J.*, 2:2143–2150 (1983).

TRANSFORMATION SYSTEM WITH TI OR RI PLASMID

This is a Continuation of U.S. application Ser. No. 07/526,123, filed May 21, 1990, now abandoned, which is a continuation of U.S. application Ser. No. 07/267,685, filed Nov. 2, 1988, now abandoned, which is a continuation of U.S. application Ser. No. 06/692,605, filed Jan. 17, 1985, now abandoned.

BACKGROUND OF THE INVENTION

1. Field of the Invention

While the ability to manipulate bacterial and mammalian cells by hybrid DNA technology has been available for almost a decade, only in 1983 was it first reported that successful expression of an exogenous gene was achieved in a plant cell. Plants have a highly complex genome and differ in numerous ways from both bacterial and mammalian genes. Therefore, while as a first approximation, one may extrapolate from the experience with other species, the relevance of such experience must be determined by experimentation.

In order to be able to successfully modify plant cells, it will be necessary to develop a large number of different systems for introducing the exogenous DNA into the plant cell, for directing, as appropriate, the introduced DNA either randomly or to particular genomic sites, to provide for constitutive or regulated expression and, as appropriate, to provide for transport of the product to an appropriate site. Toward this end, it will be necessary to develop a wide variety of regulatory signals involved with replication, transcription, translation, integration, and the like. To varying degrees; these regulatory signals will have general application across species or be species-specific, will be associated with specific stages of plant growth, or be subject to external control. To that extent, it will be necessary to develop a wide spectrum of regulatory sequences to allow for expression under predetermined conditions.

In addition, different systems may be required for the introduction of nucleic acid into plant cells to obtain reasonable efficiencies of transformation and functioning of the nucleic acid. In many instances, such as the tumor inducing plasmids and viruses, the vectors have found limited utilization in their range of hosts. Therefore, different transformation and replication systems may be required for different plant species.

2. Description of the Prior Art

Lack of transformation by Agrobacterium of soybean is reported by DeCleene and DeLey, *The Botanical Review* (1976) 42:389–466. Encouraging results in the transformation (Pederson et al., *Plant Cell Repts.* (1983) 2:201–204 and Hood et al., *Bio/Technology* (1984) 2:702–708) and regeneration (Christianson et al., *Science* (1983) 222:632–634) of soybean have recently been reported. A light inducible soybean SSU gene (small subunit SSU) of ribulose-1,5-bisphosphate-carboxylase (RuBP-carboxylase) is reported by Berry-Lowe et al., *J. Mol. Appln. Gen.* (1982) 1:483–498. Sequences 5' to pSSU gene were recently shown to direct foreign gene expression in a light-inducible manner when transferred into tobacco callus (Herrera-Estrella et al., *Nature* (1984) 310:115–120).

SUMMARY OF THE INVENTION

Novel methods and DNA constructs are provided for transforming plants employing T-DNA and a Ti- or Ri-plasmid for heterologous DNA introduction and integration into the plant genome. Transformation without gall formation of plant cells which have historically not been Agrobacterium hosts is achieved with successful expression of the heterologous DNA.

DESCRIPTION OF THE SPECIFIC EMBODIMENTS

A novel method is provided for the introduction of foreign DNA employing T-DNA from an Agrobacterium plasmid, where efficient functional introduction of heterologous DNA is achieved in plants normally considered outside the Agrobacterium range, e.g., monocotyledons and leguminous dicotyledons, without gall formation. The method can also be used with the known dicotyledon hosts of Agrobacterium. DNA constructs are made which can be inserted into an Agrobacterium plasmid for transfer to a plant host. Plant hosts of particular interest are the grains and legumes.

The DNA constructs which are provided employ T-DNA flanking regions, flanking a structural gene including transcriptional and translational regulatory sequences. In conjunction with the subject method these constructs may be used for the introduction of the structural gene into plant cells in culture, where the cells may be regenerated into whole plants.

The construct which includes the structral gene, its transcriptional and translational regulatory controls, and the T-DNA flanking regions will for the most part have the following formula:

$$(T^1)_a\text{-P-S.G.-Te-}(T^2)_b$$

wherein:

$T^1$ and $T^2$ are the same or different and are T-DNA from a Ti-plasmid or a Ri-plasmid, where a and b are 0 or 1, at least 1 of a and b being 1;

P is a promoter region recognized by a plant host, which promoter region may include promoters derived from Ti- or Ri-plasmids, such as the octopine synthase or nopaline synthase promoters, viral promoters, plant promoters, particularly leguminous and monocotyledonous plant host promoters of various structural genes, e.g., RuBP-carboxylase, more particularly SSU;

S.G. intends a structural gene having an open reading frame and having at its 5'-end an initiation codon and at its 3'-end one or more nonsense codons;

Te intends a termination region functional in the plant host cell.

The promoter region will normally include a region for binding of RNA polymerase, as well as a cap site. In addition, there may be present enhancers, operators, activators, or other regions involved with transcriptional regulation. The terminator regions, besides including at least one terminating sequence, may also include a polyA signal.

The use of T-DNA as a flanking region in a construct for integration into a Ti- or Ri-plasmid has been described in EPO Application No. 116,718 and PCT Application Nos. W084/02913, 02919 and 02920. See also Herrera-Estrella, *Nature* (1983) 303:209–213; Fraley et al., *Proc. Natl. Acad. Sci. USA* (1983) 80:4803–4807; Horsch et al., *Science* (1984) 223:496–498; and DeBlock et al., *EMBO J.* (1984) 3:1681–1689. Various fragments may be employed in the constructions to provide for homology with the T-DNA of the tumor plasmids. The homology may involve structural genes, promoter regions, other untranslated regions such as border regions, or the like.

Any structural gene of interest may be employed for use in the construct. In many instances, it will be desirable to have another structural gene to serve as a marker associated with the construct, so that one can detect those plant cells in which the foreign gene has been stably introduced. For the most part, these constructs will have the following formula:

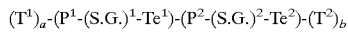

$$(T^1)_a\text{-}(P^1\text{-}(S.G.)^1\text{-}Te^1)\text{-}(P^2\text{-}(S.G.)^2\text{-}Te^2)\text{-}(T^2)_b$$

wherein:

all of the symbols have the same functional definition except that the superscripts for P and Te intend that the promoter and terminator regions may be the same or different and that the structural genes are different, where one is a marker and the other is a structural gene of interest. Of course, one may provide for a string of expression constructs having a plurality of the same or different genes in the construct. Thus, the presence of only two genes flanked by the T-DNA is merely illustrative.

As markers for structural genes, one can employ antibiotic resistance genes, e.g., a kanamycin resistance gene or methotrexate resistance gene (DHFR). These genes are described in Haas and Dowding, supra. The structural gene of interest may be any gene, either native, mutant native, or foreign to the plant host. For native and mutant native genes, the gene may provide for increased capability of protein storage, improved nutrient source, enhanced response to light, enhanced dehydration resistance, e.g., to heat, salinity or osmotic pressure, herbicide resistance, e.g., glyphosate, or the like. Foreign genes may include enhancement of native capabilities, herbicide resistance, resistance to various pests, such as viruses, insects, bacteria or fungi, production of foreign products, as a result of expression of one or more foreign genes, or the like.

In preparing the cassette construct, the various DNA sequences may normally be inserted or substituted into a bacterial plasmid. Any convenient plasmid may be employed, which will be characterized by having a bacterial replication system, a marker which allows for selection in the bacterium and generally one or more unique, conveniently located restriction sites. These plasmids, referred to as vectors, may include such vectors as pACYC184, pACYC177, pBR322, pUC9, the particular plasmid being chosen based on the nature of the markers, the availability of convenient restriction sites, copy number, and the like. One then defines a strategy which allows for the stepwise combination of the different fragments. As necessary, the fragments may be modified by employing synthetic adapters, adding linkers, employing in vitro mutagenesis or primer repair to introduce specific changes in the sequence, which may allow for the introduction of a desired restriction site, for removing superfluous base pairs, or the like. By appropriate strategies, one desires to minimize the number of manipulations required as well as the degree of selection required at each stage of manipulation. After each manipulation, the vector containing the manipulated DNA may be cloned, the clones containing the desired sequence isolated, and the vector isolated and purified. As appropriate, hybridization, restriction mapping or sequencing may be employed at each stage to ensure the integrity and correctness of the sequence.

The cassette constructs may be introduced into the plant host cell in a variety of ways, such as an insertion into a tumor- or gall-producing plasmid, as bare DNA, or as an insertion in a plant DNA virus. In accordance with the subject invention, an efficient procedure is provided for introduction of foreign DNA into plant cells with integration of the DNA and without gall formation, particularly as to plants which have previously reported to be outside the host range of Agrobacterium.

For a list of plant genera and species which are hosts and non-hosts for Agrobacterium, see De Cleene and De Ley, *The Botanical Review* (1976) 42:389–466. Of particular interest in the subject invention are dicotyledon legumes, such as soybean, and monocotyledon grains, such as corn, rice, wheat, barley and oats.

Where a tumor- or gall-producing plasmid, e.g., the Ri- or Ti-plasmid, is to be used to introduce the cassette into the plant cell, a binary plasmid, which includes an Agrobacterium functional replication system, or bacterial mating may be employed, whereby the cassette carrying plasmid is transferred from a compatible bacterium to *A. rhizogenes* or *A. tumefaciens* and the transconjugant isolated and analyzed for integration of the cassette into the Ri- or Ti-plasmid. This can be readily determined by various techniques, such as Southern analysis.

The Ti- or Ri-plasmid which is employed should be capable of providing for integration of T-DNA in the host without observable symptoms of tumor or gall formation. Thus, the plasmid which is selected may be tumor-producing in a convention host, but will not produce tumors in plants normally considered not to be hosts. An illustrative plasmid is pTiA6, a wild-type plasmid.

The *A. rhizoqenes* or *A. tumefaciens* bacteria containing the cassette and the Ri- or Ti-plasmid may now be used for transformation of a plant host cell.

The subject method employs in vitro grown seedlings between green V-E and V-1 (Fehr and Caviness, 1977, Stages of Soybean Development. Iowa Stage Coop. Ext. Serv., Agric. and Home Econ. Expt. Stn. Special Report 80). Thus, young plants, the hypocotyl or next leaf are employed. The Agrobacterium cells are injected into the plant tissue. Generally, about 1–5 $\mu$l of $1\times10^6$ to $1\times10^8$ cells/ml will be injected. Injection of Agrobacterium into cotyledons, nodes and internodes causes a visible necrosis around the wound site. No tumor formation is observed. After about one to three weeks, the explants are excised from the tissue surrounding the site of injection and subcultured in a hormone lacking medium. Callus is observed to grow from some of the explants. Opine is present in these tissues, while none is detected in non-transformed callus.

Of particular interest as a promoter is the soybean small subunit promoter. The nucleotide sequence of the small subunit gene is described by Berry-Lowe, *J. Mol. Appl. Gen.* (1982) 1:483–498. A DdeI digest of a plasmid containing a genomic fragment which includes the SSU soybean gene yields a 1.1 kb 5' piece that can be used as a promoter fragment.

By use of the soybean SSU promoter, it is found that the expression of the gene under the SSU promoter can be light-induced. Thus, the expression of the gene is regulatable, where enhanced expression occurs during irradiation with light, while substantially reduced expression or no expression occurs in the absence of light.

By virtue of having a regulatable promoter in the soybean plant, one can provide for protection against herbicides, by providing a herbicide-resistant gene to be under the regulatable control of the SSU promoter. For example, by employing a mutated aroA gene, the enzyme 5-enolpyruvyl-3-phosphoshikimate synthase which is glyphosate-resistant can be produced under light induction. Thus, the soybean plant may be protected from glyphosate, allowing for the killing of weeds employing the glyphosate herbicide. While glyphosate may be used by itself, particularly for pre-emergent spraying and post-emergent control of weeds, the glyphosate may also be used with other post-emergent broadleaf herbicides, such as Basagran (bentazan), Tackle/

Blazer (aciflurofen). Normally, applications will vary from about 0.25 to 1.5 lbs/acre, where the herbicides may be formulated as dry or wet formulations, by themselves or in combination with other additives, such as sticking agents, spreading agents, stabilizers, or the like. Inert powders may be used with dry formulations.

The following examples are offered by way of illustration and not by way of limitation.

EXPERIMENTAL

Bacterial Strains, Plasmids, and Media

E. coli strains MM294(F$^-$endA1 hsdR17 supE44 thi$^-$1) (Meselson and Yuan, Nature (1968) 217:1110–1114) and 71-18 (Δlac-proAB) supE thi F' lacI$^q$ Z M15 proA$^+$B$^+$) (Messing et al., Proc. Natl. Acad. Sci. USA (1977) 74:3642–3646) were routinely used for transformations. A. tumefaciens A348 contains the octopine Ti-plasmid pTiA6 in A114 (Garfinkel and Nester, J. Bacteriol. (1980) 144:732–743). pRK2073 was maintained in HB101(F$^-$ hsd$^5$20 (r$_B$-r$_m$-) recA13 proA2 lacY1 leuB6 rpsL20 thi 1 supE44) (Boyer and Rouland-Dussiox, J. Mol. Biol. (1969) 41:459).

Plasmid pRK2073 was generated by insertion of Tn7 into the Kan$^r$ gene of pRK2013. (Ditta et al., Proc. Natl. Acad. Sci. USA (1980) 76:1648–1652) pSRS2.1 (Berry-Lowe et al., 1982, supra.) contains a 2.1 EcoRI fragment of a soybean small subunit gene (SSU) in pBR325. The Bam19 fragment of pTiA6 was maintained as a 4.6 kb subclone in pBR325 (pNM33C-19-1) (Thomashow et al., Cell (1980) 19:729–739). pCGN464 contained the 1.5 kb HindIII-SalI fragment of Tn5 cloned into the sp6 transcription vector pSP65 (Melton et al., Nucl. Acids Res. (1984) 12:7035–7056). The pUC7 recombinant vector containing the 1.0 kb BglII-SmaI fragment of Tn5 (pCGN546) is designated pCGN546.

E. coli were grown on LB media (Miller, 1972, Experiments in Molecular Genetics, CSH Laboratory, Cold Spring Harbor, N.Y.). A. tumeficiens were grown in either minimal AB medium (Chilton et al., Proc. Natl. Acad. Sci. USA (1974) 71:3672–3676) or in MG/L (50% LB:50% mannitol-glutamate medium (Roberts and Kerr, Physiol. Plant Pathol. (1974) 4:81–91.

Soybean Transformation and Growth

Soybean (glycine max cv "forrest") seeds were surface sterilized (12 min, 5% sodium hypochlorite, 0.1% Tween 80), washed 3 times in distilled water and germinated aseptically (1/10 MS-Gibco, 0.6% phytagar (Gibco) medium without hormones, 25° C. red light (Grolux 40W)). Agrobacterium containing strains pTiCGN327 and pTiCGN609 were grown overnight (MG/L medium, 30° C.) were injected into hypocotyl, cotyledons, node and internode of two to three week old seedlings. Three weeks after injection, tissues surrounding the injection site were excised and placed on 0.6% phytagar MS medium deprived of hormones and containing 0.5 g/L carbenicillin. Hormone independent, octopine positive tissues were then transferred to liquid MS medium and analyzed for the presence of octopine (Otten and Schilperoot, Biochem. et Biophys. Acta (1978) 527:497–500). To determine kanamycin resistance, growing calli were then placed in light or complete darkness. Friable calli of light grown or dark grown 327 and 609 were disaggregated by filtering through a 105μ nylon mesh. Samples (0.1 ml packed cell volume (p.c.v.)) of fine suspensions (1–15 cells/clump) were placed in the same medium containing 0 to 300 mg/L kanamycin. Pigmented cells were kept in the light while the non-pigmented cells were kept in total darkness. The effects of kanamycin on growth were measured as packed cell volume six weeks later.

DNA Isolation

The alkali-lysis procedure of Ish-Horowitz (Maniatis et al., 1982, Molecular Cloning, A Laboratory Manual, CSH Laboratory, Cold Spring Harbor, N.Y.) was used for both large-scale plasmid isolation and for mini-prep analysis. Total DNA from A. tumefaciens was prepared as described (Currier and Nester, J. Bacteriol. (1976) 126:157–165).

DNA fragments were isolated from low melt agarose gels (Sea Plaque) run in TAE buffer (0.04M Tris-acetate, 0.002M EDTA (Maniatis, supra.) without ethidium bromide. The desired fragment was extracted from the excised agarose band by melting at 65° C. for 30 min followed by phenol extraction and ethanol precipitation.

Cloning Procedures

Restriction enzyme digestions and ligations were performed according to manufacturer's instructions. Klenow fill-in reactions and transformation were as described (Maniatis, supra.). When pUC9 was being transformed into E. coli strain 71-18, X-Gal and IPTG were added to the plates as described (Miller, 1972, supra). Correct insertion and orientation of recombinants were verified by 2 to 3 restriction digests.

The verification of the SmaI-DdeI junction in pCGN606 was done by cloning the 1.1 kb BamHI-EcoRI fragment into M13mp9 (Maniatis, supra). Sequence analysis was then performed in accordance with conventional ways.

Agrobacterium Matings

The pCGN609 construct was integrated into the Ti-plasmid pTiA6 in a three-way mating (Comai et al., 1983, supra). Overnight E. coli strains containing cultures of pCGN609 and pRK2073, respectively, were mixed with A. tumefaciens strain A722 and spread on AB plates containing 150 μg/ml kanamycin and 250 μg/ml streptomycin. Single colonies were restreaked twice. Correct integration was verified by Southern analysis of total Agrobacterium DNA. BamHI digested DNA was probed with a nick-translated 2.5 PstI-EcoRI 3' ocs fragment from pCGN607. Southern analysis and nick translation were performed in accordance with conventional ways.

RNA Preparation and Northern Blot Analysis

RNA was prepared from soybean callus by a modification of the guanidine thiocyanate procedure of Colbert et al. (Proc. Natl. Acad. Sci. USA (1983) 80:2248–2252) in which the extraction buffer contain 4M guanidine thiocyanate, 2% lauryl sarcosine, 1% β-mercaptoethanol, 50 mM Tris, pH 7.5, 20 mM EDTA, 1 mM aurintricarboxylic acid, 0.4% antifoam A (Sigma). PolyA$^+$ RNA was purified over oligo-dT cellulose (Maniatis, supra.) and Northern gels run as previously described (Shewmaker et al., 1984, supra). $^{32}$P-RNA bacterial amioglycoside phosphotransferase mRNA complementary to (APH(3')II-mRNA) (Herrera-Estrella et al., EMBO J. (1983) 2:987–995; Bevan et al., Nature (1983) 304:184–187) was synthesized from BglII cut pCGN464 using a riboprobe kit (ProMega Biotech) according to the manufacturer's instructions. The hybridization buffers were as suggested by the riboprobe manufacturer's with hybridization at 55° C. and washes at 60° C.

Kanamycin Activity Blots

The kanamycin activity blots (Reiss et al., *Gene* (1984) 30:211) were performed as modified for plants (Schreier et al., *EMBO J.* (1985) 4:25–32). For each sample, 0.2 g of fresh soybean callus was used.

Construction of Soybean ssu-Kan$^r$ Chimera

A soybean SSU gene (Berry-Lowe, 1982, supra) was chosen as the source of the 5'-promoter region. In this gene there is a DdeI site, 9 bp upstream of the AUG. A DdeI digest of pSRS2.1 (Berry-Lowe, 1982, supra.) yielded a 1.1 kb 5' fragment isolated out of a low melt agarose gel. The 5' 1.1 kb DdeI fragment was filled in with Klenow polymerase and ligated into SmaI digested pUC9 (Vieira and Messing, *Gene* (1982) 19:259). A clone, pCGN606 was obtained that had the SSU promoter facing the adjacent EcoRI site of pUC9.

A cassette containing the soybean 5' region and an appropriate 3' region was then constructed. For this cassette, the octopine synthetase (ocs) 3' region was chosen as a 2.5 kb EcoRI-PstI fragment from a Bam19 subclone of pTiA6 (Thomashow, 1980, supra). Since it contained regions homologous to T-DNA, it would facilitate transfer to the Ti-plasmid of Agrobacterium. The cassette pCGN607 was obtained in a 3-way ligation with this fragment, the 1.1 kb BamMI-EcoRI 5' soybean SSU fragment from pCGN606, and the 2.7 kb BamHI-PstI fragment of pACYC177 (Chang and Cohen, *J. Bacteriol.* (1978) 134:1141).

The APH(3')-II gene employed was from Tn5, which confers resistance to kanamycin both in bacteria (Haas and Dowding, *Meth. Enzymology* (1975) 43:611–628) and plants (Herrera-Estrella, 1983, supra). A 1.0 kb BglII-SmaI fragment containing the gene was cloned into pUC7 resulting in adjacent flanking EcoRI restriction sites. The plasmid was digested to provide a 1.0 kb EcoRI fragment and this fragment ligated into EcoRI digested pCGN607. Clones were screened for those carrying the Kan$^r$ gene of Tn5 in the correct orientation. One of the clones which had the correct orientation was designated pCGN609. The plasmid also carried the kanamycin resistance gene from pACYC177 (APH(3')-I) as a bacterial marker. These two kanamycin resistance genes (APH(3')-I and -II) do not cross-hybridize at the nucleic acid level.

Following Klenow polymerase fill-in, only 9 bp which are present upstream of the AUG in native soybean SSU are lacking in pCGN609. These 9 bp are replaced with 46 bp that arise from the fusion manipulations. The rest of the 1.1 kb soybean SSU 5' region is the same in pCGN609 as in native soybean.

The integration of pCGN609 into the Ti-plasmid pTiA6 was accomplished in a three-way (Comai et al., 1983) mating with pRK2073. Correct integration was verified by Southern analysis of the resulting Agrobacterium, designated pTiCGN609. In the integration an intact octopine synthetase region is maintained as evidenced by the detection of octopine. Octopine was detected by fluorescence of its phenanthroquinone adduct following paper electrophoresis of tissue extracts (10 mg).

Transformation of Soybean

Transformation of soybean was performed on in vitro grown seedlings from the time their cotyledons turned green up to the time of the appearance of the second internode. In every case, the injection of Agrobacterium caused a clearly visible necrosis around the wound site. Occasionally, after 1 to 3 weeks, roots would appear at the innoculation site. Splitting also occurred, revealing swollen tissue, but in no case was tumor noted with the Agrobacterium strains used. Explants excised from the tissue surrounding the site of injection were subcultured in MS medium deprived of hormones, 0.6% phytagar, 0.5 g/L carbenicillin. Hormone-independent callus grew from some of the explants. Hormone-independent growing tissue was transferred to MS medium. Analysis of this tissue for the presence of octopine was positive, while no octopine was detected in non-transformed soybean tissue. All aerial parts of th soybean seedlings, cotyledons, internodes, and nodes, were able to produce transformed tissue although no systematic study was done to determine which of these areas is most susceptible to Agrobacterium.

Analysis of polyA$^+$ RNA in Light and Dark Grown Tissue

The increase in SSU protein seen in a number of light grown plants was shown to correlate with an increase in the level of SSU polyA$^+$ RNA. Northern analysis of light and dark grown 609 soybean callus was performed to determine if an increase in APH(3')-II polyA$^+$ RNA occurred with growth in light. The results were determined with a $^{32}$P-RNA probe specific for APH(3')-II transcript in the sense orientation. An RNA of the expected size of approximately 1.6 kb was seen in both cases of light and dark. Approximately 5–10 times as much transcript was seen in the light grown tissue as the dark grown tissue.

Presence of Protein with Kanamycin Phosphotransferase Activity

APH(3')-II (aminoglycoside phosphotransferase) inactivates kanamycin by phosphorylation. The presence of this activity can be demonstrated by a number of assays which measure the phosphorylation of kanamycin in vitro. In the assay employed (Reiss et al., *Gene* (1984) 30:211) extracts are run on an acrylamide gel, reacted in situ with kanamycin and $\gamma$-$^{32}$P-ATP and then blotted to P81 (phosphocellulose) paper. For green (light grown) and white (dark grown) 609 soybean callus, activity was seen in the green soybean at the same mobility as that observed for purified APH(3')-II, while no detectable activity was seen in white 609 tissue or in soybean transformed with an Agrobacterium lacking the APH(3')-II gene.

Demonstration of Kanamycin Resistance in the Transformed Tissue

Greening of the soybean callus occurred spontaneously after exposure to light. Some of the green 609 callus selected for its friability was disaggregated as described previously and used to analyze its resistance to kanamycin. It was compared to similar non-pigmented tissue grown in complete darkness. Dark grown 609 as well as control 327 tissue died in the presence of 50 mg/L kanamycin, while the light grown tissue could survive up to 300 mg/L kanamycin although its growth was slightly inhibited at this concentration.

It is evident from the above results that not only can soybean be transformed, so as to introduce heterologous genes, but transformed soybean cells may be regenerated into plants and the plants demonstrate the phenotype of the heterologous gene. In addition, native promoters can find use in conjunction with heterologous genes and retain their capability to be induced in the same manner as the native gene. Therefore, one can provide for regulated expression of a heterologous gene, where regulation may be by an external condition, such as light. Furthermore, Ti- or Ri-DNA may be employed for introducing the heterologous gene as part of an expression cassette into the soybean cell without formation of a tumor and the resulting cells grown in culture and plants regenerated from the cells. By appropriate choice of various genes, various properties of the cell may be enhanced by introduction of additional copies of a homologous gene or new phenotypes may be provided by expression of heterologous genes. In addition, mutated genes may be employed which can impart novel properties to the host cell, providing for host resistance to biocides, enhanced production of specific metabolites or products at the same or different times from the normal regulated expressions, or the like.

Although the foregoing invention has been described in some detail by way of illustration and example for purposes of clarity of understanding, it will be obvious that certain changes and modifications may be practiced within the scope of the appended claims.

What is claimed is:

1. A non-gall soybean cell having integrated in its genome a DNA construct, said construct comprising a promoter region functional in said soybean cell upstream from a structural gene foreign to said promoter region and a termination region functional in said soybean cell downstream from said structural gene, wherein said DNA construct is flanked by non-disarmed T-DNA comprising tumor inducing genes.

2. A cell according to claim 1, wherein said promoter region is an SSU promoter.

3. A cell according to claim 2, wherein said promoter region is a soybean SSU promoter.

4. A cell according to claim 1, wherein said structural gene expresses an enzyme.

5. A cell according to claim 4, wherein said enzyme provides for biocide resistance.

6. A cell according to claim 5, wherein said biocide is kanamycin.

7. A cell according to claim 6, wherein said cell is resistant to kanamycin at concentrations up to 300 milligrams per liter.

8. A soybean cell according to claim 1, wherein said structural gene is a kanamycin resistance gene.

* * * * *